US006495338B1

(12) United States Patent
Rohrwasser et al.

(10) Patent No.: US 6,495,338 B1
(45) Date of Patent: Dec. 17, 2002

(54) DRUG SCREENING AND DIAGNOSIS BASED ON PARACRINE TUBULAR RENIN-ANGIOTENSIN SYSTEM

(75) Inventors: Andreas Rohrwasser, Salt Lake City, UT (US); Terry Morgan, Salt Lake City, UT (US); Jean-Marc Lalouel, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/389,242

(22) Filed: Sep. 3, 1999

Related U.S. Application Data
(60) Provisional application No. 60/099,270, filed on Sep. 4, 1998.

(51) Int. Cl.$^7$ ................................................. C12Q 1/37
(52) U.S. Cl. ............................... 435/23; 436/86; 514/2; 530/316; 424/94.66
(58) Field of Search ........................... 514/2; 530/316; 424/94.66; 436/86; 435/23

(56) References Cited

PUBLICATIONS

Yoshiya et al. "Angiotensinogen Excretionin Rat Urine: Effects of Lipopolysaccharide Treatment and Sodium Balance", Japan. J. Pharmacol. vol. 57, pp. 37–44 (1991).*
File Medline on STN. An No. 88316609. Iwamoto et al. "Effect of Sodium Intake on Urinary Renin Excretion in Rats." Journal of Pharmacobio–Dynamics, vol. 11, No. 4, pp. 245–250. Abstract only. (Apr. 1988).*
Ferrario et al. "Characterization of Angiotenisn–(1–7) in teh Urine of Normal and Essential Hypertensive Subjects." American J. Hypertension, vol. 11, No. 3, pp. 137–146. (Feb. 1998).*
Tank, J.E. et al. (1997). "Regulation of glomerular and proximal tubule renin mRNA by chronic changes in dietary NaCl," *Am. J. Physiol.* 273:F892–F898.
Loghman–Adham, M. et al. (1997). "A conditionally immortalized cell line from murine proximal tubule," *Kidney Internat . .* 52:229–239.
Moe, O.W. (1997). "Sodium–hydrogen exchange in renal epithelia: mechanisms of acute regulation," *Curr. Opin. Nephrol. Hypertens.* 6:440–446. (Abstract).
Navar, L.G. et al. (1997). "Intrarenal production of angiotensin II," *Semin. Nephrol.* 17:412–422. (Abstract).
Tank, J.E. et al. (1996). "Differential regulation of rat glomerular and proximal tubular renin mRNA following uninephrectomy," *Am. J. Physiol.* 270:F776–F783.
Henrich, W.L. et al. (1996). "Renin Regulation in Cultured Proximal Tubular Cells," *Hypertension* 27:1337–1340.
Wang, T. et al. (1996). "Effects of angiotensin II on electrolyte transport in the early and late distal tubule in rat kidney," *Am. J. Physiol.* 271:F143–F149.

Wang, T–T. et al. (1994). "Isoproterenol and 8–bromo–cyclic adenosine monophosphate stimulate the expression of the angiotensinogen gene in opossum kidney cells," *Kidney Internat.* 46:703–710.
Tojo, A. et al. (1994). "Angiotensin II regulates H$^{30}$ – ATPase activity in rat cortical collecting duct," *Am. J. Physiol.* 267:F1045–1051.
Yang, G. et al. (1994). "Functional expression of the human angiotensinogen gene in transgenic mice," *J. Biol. Chem.* 269:32497–32502. (Abstract).
Vos, P.F. et al. (1994). "The origin of urinary angiotensins in humans," *J. Am. Soc. Nephrol.* 5:215–223. (Abstract).
Moe, O.W. et al. (1993). "Renin Expression in Renal Proximal Tubule," *J. Clin. Investigat.* 91:774–779.
Vos, P.F. et al. (1993). "Effects of Enalapril on Renal Sodium Handling in Healthy Subjects on Low, Intermediate, and High Sodium Intake," *J. Cardiovas. Pharmacol.* 22:27–32.
Jeunemaitre, X. et al. (1992). "Molecular Basis of Human Hypertension: Role of Angiotensinogen," *Cell* 71:169–180.
Yanagawa, N. et al. (1991). "Production of angiotensinogen and renin–like activity by rabbit proximal tubular cells in culture," *Kidney Internat.* 39:938–941.
Yoshiya, M. et al. (1991). "Angiotensinogen Excretion in Rat Urine: Effects of Lipopolysaccharide Treatment and Sodium Balance," *Japan J. Pharmacol.* 57:37–44.
Cogan, M.G. (1990). "Angiotensin II: A Powerful Controller of Sodium Transport in the Early Proximal Tubule," *Hypertension* 15:451–458.
Ingelfinger, J.R. et al. (1990). "In Situ Hybridization Evidence for Angiotensinogen Messenger RNA in the Rat Proximal Tubule," *J. Clin. Invest.* 85:417–423.
Ingelfinger, J.R. et al. (1990). "Intrarenal angiotensinogen: localization and regulation," *Pediatr. Nephrol.* 4:424–428. (Abstract).
Liu, F–Y. et al. (1988). "Angiotensin II Stimulation of Hydrogen Ion Secretion in the Rat Early Proximal Tubule," *J. Clin. Invest.* 82:601–607.
Ingelfinger, J.R. et al. (1986). "Sodium Regulation of Angiotensinogen mRNA Expression in Rat Kidney Cortex and Medulla," *J. Clin. Invest.* 78:1311–1315.
Taugner, R. et al. (1984). "Coexistence of renin and angiotensin II in epitheloid cell secretory granules of rat kidney," *Histochemistry* 81:39–45.
Taugner, R. et al. (1982). "Vascular and Tubular Renin in the Kidneys of Mice," *Histochemistry* 75:473–484.
Taugner, R. et al. (1982). "The Intrarenal Renin–Angiotensin–System," *Klin Wochenschr.* 60:1218–1222.
Celio, M.R. et al. (1981). "Renin in the Human Kidney," *Histochemistry;* 72:1–10.

* cited by examiner

*Primary Examiner*—Christopher S. F. Low
*Assistant Examiner*—Anish Gupta
(74) *Attorney, Agent, or Firm*—Fish & Richardson PC

(57) ABSTRACT

The present invention relates to a method for screening drugs for use in treating hypertension using the tubular renin-angiotensinogen system identified by the present invention. The invention further relates to a method to diagnose sodium status and sensitivity in an individual by measuring urinary angiotensinogen or angiotensin-I.

2 Claims, 5 Drawing Sheets

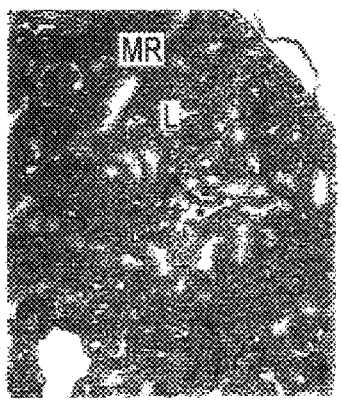 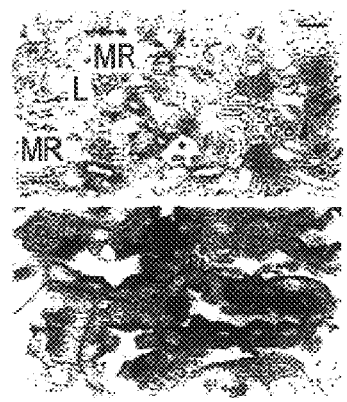
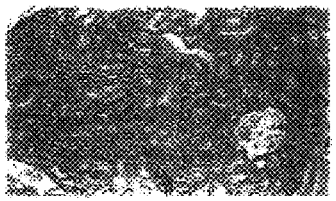 
 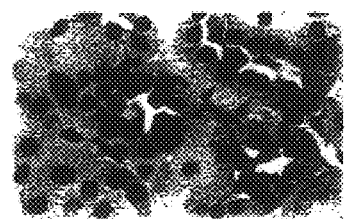

DRUG SCREENING AND DIAGNOSIS BASED ON PARACRINE TUBULAR RENIN-ANGIOTENSIN SYSTEM

CROSS-REFERENCE TO RELATED APPLICATION

The present application is related to U.S. provisional patent application Ser. No. 60/099,270 filed Sep. 4, 1998, incorporated herein by reference.

This invention was made with Government support under Grant No. HL45325 awarded by the National Institutes of Health, Bethesda, Md. The United States Government has certain rights in the invention.

BACKGROUND OF THE INVENTION

The present invention relates to a method for screening drugs for use in treating hypertension using the tubular renin-angiotensinogen system identified by the present invention. The invention further relates to a method to diagnose sodium status in an individual by measuring urinary angiotensinogen, angiotensin-I, des-AI-angiotensinogen or renin.

The publications and other materials used herein to illuminate the background of the invention, and in particular, cases to provide additional details respecting the practice, are incorporated by reference, and for convenience are referenced in the following text by author and date and are listed alphabetically by author in the appended list of references.

The following abbreviations are used herein: A-I-angiotensin-I; A-II-angiotensin-II; ACE-angiotensin converting enzyme; AGT—angiotensinogen gene; ANG or Ang—angiotensinogen protein; -6(A)/-6(G)—promoter polymorphism at position -6; CCD—cortical collecting duct; CNT—cortical connecting tubule; DCT—distal convoluted tubule; IC—intercalated cells; JGA—juxtaglomerular apparatus; PCR—polymerase chain reaction; RAS—renin-angiotensin system; RT-PCR—reverse transcriptase polymerase chain reaction; and HPLC—high pressure liquid chromatography.

Blood pressure control is intrinsically linked to fluid volume balance and electrolyte homeostasis. Regulation of plasma volume in response to variation in dietary sodium (1) is primarily controlled by the renin-angiotensin system (RAS) and its main effector angiotensin-II (A-II); this peptide hormone is released from angiotensinogen (Ang) by two cleavage steps involving renin and angiotensin-converting enzyme (ACE) (2).

The short-term effects of A-II are better understood than its long-term effects. Acute depletion of body fluid volume triggers a vasoconstrictor response mediated by the circulating renin-angiotensin system (RAS), involving renin secreted by the juxtaglomerular apparatus (JGA) in the kidney, Ang from liver, and ACE present in the luminal cell membrane of capillary endothelium.

Sustained low-dose infusion of A-II leads to progressive, long-term elevation of arterial pressure due to cumulative sodium retention primarily mediated by direct intrarenal A-II effects [1]. A-II has been detected in proximal tubular luminal fluid at high concentrations (3, 4). In contrast to plasma renin (36–40 kDa), Ang (61–65 kDa) is not filtered through the glomerular basement membrane. Detection of abundant angiotensinogen mRNA in proximal tubule epithelium (5–7), strongly suggests local generation of A-II at this site by an as yet unspecified mechanism. Renin mRNA can be detected in proximal tubule only by application of the very sensitive technique of RT-PCR (8). Exogenous A-II stimulates the luminal sodium-hydrogen exchanger present in the proximal tubule cells (9, 10) and also stimulates epithelial sodium channels and possibly other transporters in the distal segments of nephron (11–14).

Fundamental questions remain unanswered, however. If intrarenal A-II directly affects sodium reabsorption, where is it generated, and by what mechanism? How is this mechanism regulated in response to sodium? At what sites does A-II impact on sodium transport along the nephron? What is the mechanism for coordinated regulation of sodium uptake in proximal and distal segments of the nephron? Can it allow for a decoupling of sodium reabsorption and potassium excretion in the distal tubule?

It is desired to address these questions and to elucidate answers which can be used for screening drugs and diagnosing sodium status of an individual.

SUMMARY OF THE INVENTION

In accordance with the present invention, it is shown that proximal tubule cells cultured as a polarized monolayer secrete Ang at their apical side, and that Ang transits through the entire nephron as it can be measured in final urine. Furthermore, it is shown that renin, in addition to being filtered, is expressed in a specific segment of the nephron, the connecting tubule. Furthermore, angiotensinogen expression in proximal tubules and renin expression in connecting segments (distal arcades) is an inverse function of dietary sodium.

The data disclosed herein suggest that filtered renin, Ang secreted into proximal tubule, and renin in connecting tubule, together with luminal angiotensin-converting enzyme (ACE) and A-II receptors, previously demonstrated in the luminal fluid and the apical cellular membranes of proximal tubules and collecting ducts (15, 16), define a tubular RAS involved in the control of sodium reabsorption as a function of dietary salt. This tubular RAS could contribute to body fluid control and blood pressure regulation. Furthermore, genetic differences in the angiotensinogen gene (17, 18) may influence susceptibility to essential hypertension through their impact on this tubular system.

Thus, the present invention relates to a method for screening drugs for use in treating hypertension using the tubular renin-angiotensinogen system identified by the present invention. The invention further relates to a method to diagnosis sodium status in an individual by measuring urinary angiotensinogen, angiotensin-I, des-AI-angiotensinogen or renin.

It has been discovered that angiotensinogen, its enzyme catalyzed products or renin excreted in urine vary with changes in dietary sodium. Thus, the sodium status of an individual is diagnosed by determining the amount of angiotensinogen or its enzyme catalyzed products or renin in the urine of the individual and comparing the determined amount with normal values. A finding of elevated levels of these compounds indicates high sodium. An individual's sodium sensitivity can also be determined by determining the amounts of these compounds in urine. Levels of these compounds are determined using conventional techniques, and any appropriate method is suitable for use. If the levels are elevated in an individual under a high salt diet compared to reference values, the individual is sensitive to salt.

It has also been found that the expression of angiotensinogen and renin is regulated at specific sites along the kidney. This finding identifies new therapeutic targets for the blood pressure control and provides the basis for a method to screen drugs for use in treating hypertension. According to the present invention, drug candidates for treating hypertension are screened using the tubular renin-angiotensin system by testing the effects of drug candidates at the proximal and/or distal tubule.

BRIEF DESCRIPTION OF THE FIGURES

The file of this patent contains at least one drawing executed in color. Copies of this patent with color drawing (s) will be provided by the Patent and Trademark Office upon request and payment of the necessary fee.

FIG. 1A shows localization of angiotensinogen in the nephron of sodium-restricted mice. Immunostaining for angiotensinogen is observed only in proximal tubule cells, identified by PAS counterstaining. High magnification reveals an apical vesicular staining of Ang under the brush border, suggesting a secretory process. FIG. 1B shows directional secretion of Ang by proximal tubular epithelium in vitro. Western blot analysis using a polyclonal Ang antibody demonstrates that proximal tubule cells secrete angiotensinogen exclusively at their apical side. FIG. 1C shows angiotensinogen secretion, measured as urinary Ang (black bars) and urinary angiotensin-I (A-I; white bars) is an inverse function of sodium status. Ang was measured as the amount of A-I released in a cleavage reaction by renin; A-I was measured by RIA (means±S.E.M. of three replicates). FIG. 1D shows uncleaved native angiotensinogen was also detected in the urine of six healthy male human subjects.

FIGS. 2A–2G show immunolocalization of renin in connecting tubule (CNT) cells. In FIGS. 2A and 2B, tubular renin staining (arrowheads) is localized to arcades of connecting tubules of midcortical and deep nephrons. Arcades are located in the midcortical labyrinth (L) in between the medullary rays (MR) and in the vicinity of radial veins (*). Renin staining is also observed in JGA (arrow). FIG. 2C is a close-up view of CNT cells showing apical renin staining. In FIG. 2D, specificity of renin staining is demonstrated by adsorption of the renin antibody with purified mouse renin, eliminating all renin immunostaining. FIG. 2E shows that, in humans, immunoreactive rerin is also present in cells of the early cortical collecting duct. In FIGS. 2F and 2G, renin immunostaining is restricted to principal CNT cells. Serial sections were stained for renin (FIG. 2F) or for H'ATPase (FIG. 2G), a marker of intercalated cells. Renin (arrow) was not expressed in H-ATPase positive cells (arrowhead); staining was mutually exclusive (scale bar A, C=128 µm; B, D-F=20 µm).

FIG. 3E shows renin transcription detected by RT-PCR in microdissected CNT arcades. Under normal sodium diet, renin amplification products were observed unambiguously in total kidney RNA, RNA from glomeruli (glomer) and RNA from CNT arcades. In sodium-restricted animals, specific signal was strong in glomeruli and CNT arcades and faint in proximal tubules (PCT). GAPDH served as an internal control.

FIG. 3F shows a positive control section without DNase treatment, showing uniform perinuclear staining. In FIG. 3G, genomic amplification products were detected in cells of all kidney segments, including glomerulus (*), proximal tubule (arrowhead), and distal nephron segments (arrow). In FIG. 3H, negative control sections, DNase treated and with specific primers but without reverse transcription, show no renin amplification product. FIGS. 3I–3K show DNase-treated and reverse transcribed sections, revealing specific renin staining in CNT cells (arrow), but not in proximal tubule (arrowhead) or other tubular segments. In FIG. 3J, high magnification reveals positive staining in a subset of CNT cells (arrow) but not in the proximal tubule (arrowhead). In FIG. 3K, renin mRNA was also detected in juxtaglomerular smooth muscle cells (arrow). All sections were counterstained with PAS (A-C, scale bar=64 µm; D-F, bar=20 µm; F-H, scale bar=64 µm; I-K, bar=20 µm).

In FIG. 3L, a subpopulation of CNT cells from microdissected CNT arcades (arrowheads) shows pericellular halos of immunoreactive renin; non-renin producing cells are indicated with asterisks. In FIG. 3M, CHO cells expressing renin served as positive control.

In FIG. 4A, renin staining (arrows) of afferent arterioles and CNT is minimal following sodium loading. In FIG. 4B, only CNT renin staining increased following sodium loading in combination with amiloride administration. FIG. 4C shows that sodium restriction also significantly increased renin staining in CNT cells (scale bars=64 µm). Quantitative immunohistochemistry of renin expression in CNT cells (FIG. 4D) and renin expression in JGA cells (FIG. 4E) by semiquantitative RT-PCR further confirm these observation (mean±S.E.M. of four independent sets of experiments).

DETAILED DESCRIPTION OF THE INVENTION

Figure 1A:
FIGS. 1A, 1B, 1C and 1D show synthesis and secretion of angiotensinogen (Ang) in the nephron.

The present invention relates to a method for screening drugs for use in treating hypertension using the tubular renin-angiotensinogen system identified by the present invention. The invention further relates to a method to diagnose sodium status in an individual by measuring urinary angiotensinogen, angiotensin-I, des-AI-angiotensinogen or renin.

Definition of Sodium Sensitivity

Epidemiology, physiology, pathology and drug response indicate that essential hypertension encompasses a variety of conditions of unknown cause that cannot be resolved on clinical grounds alone. An important physiological distinction is whether or not sodium salt plays a significant contribution to disease. A dominant hypothesis is that there are innate differences in individual response to excess dietary sodium, and this factor would account for a significant proportion of cases of essential hypertension. This class can be defined a "sodium sensitive" hypertension simply to stress the role of this contributing factor in the development of high blood pressure.

While the significance of sodium in the epidemiology of essential hypertension is compelling in the aggregate, the relationship between sodium consumption and blood pressure has been difficult to establish at the individual level. A variety of protocols have been designed in an attempt to identify individuals who would be particularly vulnerable to excess sodium consumption. Typical maneuvers include blood pressure or weight response to a standardized sodium load. Another approach has been to monitor change in renal blood flow after infusion of angiotensin-II in individuals exposed to a high sodium diet, or similar physiological manipulations. In general, these approaches have confirmed that there are indeed two broad classes of responses to such maneuvers, some response or none, leading to the definition of "sodium sensitive" and "sodium resistant" individuals. The overlap between the two groups remains so large, however, that it precludes the unambiguous identification of any particular individual as a member of either group. This diagnosis issue has been particularly vexing for medical practice, as the efficacy of either dietary sodium restriction or specific therapeutic intervention critically depends on the identification of this underlying factor.

Sodium sensitivity, then, measures an individual's propensity to respond to excess sodium intake by an increase in either blood pressure or weight. In the context of a chronic condition such ss essential hypertension, which develops insidiously over decades, and where the adverse consequences of excess sodium intake are reflecting minimal but cumulative attrition over time, it is not altogether surprising that such a differential in chronic response escapes characterization by an acute maneuver. Related concepts will be defined below.

Sodium homeostasis subsumes the overall mechanism by which the body regulates the fate of sodium as a function of physiological needs. Sodium balance represents the net difference between intake and excretion which, on average, is zero. In certain situations, such as pregnancy or after significant blood loss, intake exceeds excretion to accommodate volume expansion or reexpansion. Sodium status, although almost synonymous with sodium balance, is generally used to characterize dietary sodium status, namely sodium excess, normal sodium, or restricted sodium intake. Monitoring sodium status is important before performing clinical maneuvers as described above, or more relevant yet to monitor compliance to dietary sodium restriction. If genetic differences contribute to sodium sensitivity, then it would be clearly of clinical relevance to characterize sodium sensitivity as a genetic "liability," or an innate predisposition to develop high blood pressure.

Significance of Intrarenal A-II in Regulation of Sodium Balance

The link inferred between angiotensinogen and sodium homeostasis results from its known physiological function. Angiotensin-II (A-II), generated exclusively from angiotensinogen protein (ANG) through two steps of enzymatic cleavages catalyzed by renin and angiotensin-converting enzyme (ACE), exerts short-term and long-term effects on vascular tone and blood volume and, as a result, it is a major determinant of blood pressure. As we argue here, the short-term effects of A-II are better understood than are its long-term effects.

The former reflects the vasoconstrictor effect of A-II at the systemic level. Specifically, renin made by a specialized segment of afferent renal arteries (called the juxtaglomerular apparatus, or JGA) acts in the general circulation on angiotensinogen released by the liver to form angiotensin-I (A-I), subsequently converted to A-II by ACE in capillary vessels. Increased circulating A-II would then induce constriction of arterioles that regulate peripheral vascular resistance and the overall compliance of the vascular system. When blood volume is depleted, the net effect of reduced compliance is maintenance of normal blood pressure. When blood volume is normal, increased vascular resistance leads to increased arterial pressure.

The characterization of the long-term effects of A-II has proven far more elusive. Reexpansion of blood volume after depletion requires sodium retention in the kidney (as water "follows" sodium). Under normal conditions, variation in dietary sodium intake leads to compensatory adjustment of sodium excretion so as to maintain baseline blood pressure within narrow limits. A-II has been recognized as the dominant hormone promoting sodium retention, through both indirect and direct renal effects.

Indirect effects of A-II are mediated by aldosterone, a mineralocorticoid (a steroid affecting mineral metabolism) released by the adrenal after A-II stimulation. This hormone acts in the distal part of the nephron where it promotes sodium reabsorption and potassium excretion. Most textbooks still emphasize the presumed dominance of aldosterone in promoting sodium retention.

The direct sodium-retaining effects of A-II in the kidney are multiple and varied, affecting both renal hemodynamics, that is, the regulation of blood flow through various parts of the kidney, and the activity of sodium transporters mediating reabsorption of filtered sodium. These direct effects have been primarily demonstrated by addition of A-II to experimental preparations, and as such, these experiments have not clarified the actual origin, site of action, and regulation of A-II accounting for such effects.

A large body of experimental evidence accumulated over the last two decades has demonstrated that, in normal physiological states, aldosterone plays only a modest role in regulation of sodium excretion to balance intake. Rather, this function is primarily mediated by intrarenal A-II.

A Paracrine Tubular Renin-Angiotensin System

The essence of the findings described here is as follows:

(1) Angiotensinogen is secreted into tubular fluid by epithelial cells of the proximal tubule (cells lining the luminal side of this nephron segment).

(2) AGT expression at this site is a function of sodium status.

(3) Angiotensinogen protein transits through the entire nephron and can be measured in urine, where it results from proximal tubule secretion (circulating angiotensinogen is not filtered through the glomerular membrane, by contrast to renin).

(4) Renin is expressed by principal cells of the distal nephron, the very cells expressing both sodium channel (for sodium reabsorption) an potassium channel (for potassium secretion under control of aldosterone).

(5) Renin expression at this site also varies as a function of sodium status.

(6) Blocking the sodium channel of principal cells with amiloride leads to up-regulation of renin expression in distal nephron, indicating that sodium translocated by this channel is an important sensing mechanism in the regulation of renin expression in distal nephron.

(7) A-I and active renin, reflecting activity of distal nephron, can be measured in urine.

Proposed Function of This Paracrine System

Massive amounts of sodium are filtered daily, of which 99%, to almost 100% are reabsorbed by the kidney ("Sodium Balance"). Different transporters are involved in various segments of the nephron ("Sodium Transporters"), and coordination of the activity in each segment determines the final amount of sodium excreted in final urine. It is common to contrast the functions of proximal and distal tubule as "bulk" and "fine" sodium reabsorption, respectively. After a bulk phase where the majority of filtered sodium, water and various solutes are reabsorbed together by a global process dominated by sodium movement, a fine phase allows independent, fine adjustment of each constituent in final urine. Angiotensinogen expression in proximal tubule suggested its involvement in the bulk phase, but did not provide a mechanism for a more critical role in final adjustment of urinary sodium.

The paracrine system described herein provides an answer. It reveals the mechanism by which the renin-angiotensin system regulates sodium excretion by integrating function at these two critical sites. The concept is novel, and it has extensive implications for diagnosis therapeutic research. The diagnostic implications will be detailed, rather briefly given previous claims and the background given here.

As shown by the examples below, it has been found that proximal tubular epithelium cells synthesize and secrete angiotensinogen, that angiotensinogen circulates through the entire nephron and can be detected in urine, that renin is expressed by principal cells of the distal nephron, and that expression of substrate and enzyme at these sites is affected by variation in dietary sodium. This previously unidentified tubular renin-angiotensin system provides the basis for the drug screening method of the present invention.

A large number of pharmaceutical drugs have been developed and are used as antihypertensive agents. They can be classified into broad subclasses as a function of their principle of action and the biochemical function they target. As noted above, the renin-angiotensin system (RAS) is of fundamental importance in blood pressure control. The most recent drugs developed in the field interfere with this system in one of at least three ways. Renin inhibitors are analogs of the angiotensinogen cleavage site which bind to renin with high affinity, and as such, compete with angiotensinogen. Although effective, these compounds have been of limited usefulness because of problems in drug delivery. ACE inhibitors, such as captopril or lisinopril, have proven effective and have become one of the drugs of choice in the treatment of essential hypertension. The A-II Type 1 receptor inhibitor, Losartan from Dupont-Merck, represents the newest agent developed to counter the physiological effects of A-II. Its high affinity for the major receptor mediating the hemodynamic effects of A-II accounts for its action.

A common feature of these drugs designed to interfere with the RAS is that they have global, systemic and local effects. Indeed, given the preeminent role ascribed to the circulating RAS in research preceding the development of these agents, they reflect the state of knowledge of the time at which drug development was developed in these directions.

The results described herein pertaining to the existence and the role of a paracrine tubular RAS in the regulation of sodium balance suggest new targets for therapeutic intervention and new methods to screen compounds and ascertain their biological effectiveness.

Thus, the present invention identifies novel targets for the development of antihypertensive agents. The new agents will primarily interfere with the normal function of the paracrine tubular RAS we describe at either the proximal tubule or in the distal nephron. Compounds can be engineered so as to be delivered at either site and so that their biological activity is optimal under the prevailing environment of each segment. The net effect is to control sodium reabsorption, and as such, it will prevent the development of essential hypertension in subjects deemed sodium sensitive. The drugs may prove most effective in a subset of hypertensive patients. Together with means to identify such subjects, as we have claimed with AGT the selectivity and specificity of such drugs will alleviate the difficulty of choosing a given drug and determining effective dosage. It is recognized that any given drug is effective in only a fraction of patients, and at present, there is no simple way of predicting if any given patient will respond well to any particular agent. Indications may be based on associated manifestations, such as coronary heart disease, but not on actual knowledge about the mechanism accounting for hypertension. Both conditions being common, there must be instances where hypertension depends on factors distinct from those accounting for coronary disease.

In addition, screening methods are used to determine the efficacy of compounds designed so as to interfere with the renin-angiotensin system at either the proximal or distal tubule. The effects of these compounds can be monitored at three levels: cellular, tissue and whole organism. In the proximal tubule, cellular response to drugs can be monitored in terms of angiotensinogen expression and secretion or in terms of sodium transport by the sodium-hydrogen exchanger and other sodium-dependent transporters. In the distal tubule, targeted drugs will affect the activity of the sodium channel, the density of A-I receptors, and the synthesis and release of renin by principal cells. At the tissue level, expression of angiotensinogen and renin can be monitored by any one of the methods described herein, including in situ RT-PCR, RT-PCR of microdissected nephron segments, particularly Y-junctions, and immunohistochemistry. At the level of the entire organism, the efficacy of compounds can be evaluated by measuring parameters of the paracrine RAS in urine, including A-I and A-II total angiotensinogen, des-AI-angiotensinogen, uncleaved angiotensinogen, total renin and renin activity. Furthermore, the effects of such agents on blood pressure and plasma volume can be monitored.

As shown by the examples below, it has been found that angiotensinogen, its enzyme catalyzed products or renin excreted in urine vary with changes in dietary sodium. Thus, the sodium status of an individual is diagnosed by determining the amount of angiotensinogen or its enzyme catalyzed products or renin in the urine of the individual and comparing the determined amount with normal values. Any method for detecting urinary angiotensinogen or angiotensin-I can be used in accordance with the present invention. A finding of elevated levels of these compounds indicates high sodium. The levels of these compounds are determined using conventional techniques and any appropriate method is suitable for use. An individual's sodium sensitivity can also be determined by determining the amounts of these compounds in urine. If the levels are elevated in an individual under a high salt diet compared to reference value, the individual is sensitive to salt.

It has also been found that expression of angiotensinogen and renin is regulated at specific sites along the kidney. This finding identifies new therapeutic targets for blood pressure control and provides a basis for a method to screen drugs for use in treating hypertension. According to the present invention, drug candidates for treating hypertension are screened using the tubular renin-angiotensin system by testing the effects of drug candidates at the proximal and/or distal tubule.

Molecular variants in the angiotensinogen gene (AGT) may reflect individual predisposition to the development of essential hypertension, as we claimed earlier with t235 and a(−6) variants. The actual manifestation of the genetic propensity evidently depends on the degree and the duration of the exposure to high sodium intake as well as other promoting factors such as overweight and excess stress.

Angiotensinogen, A-I and active renin can be measured in urine in animals and humans. Furthermore, the amount of angiotensinogen detected in urine reflected sodium status. It was at the limits of detection under high sodium diet, but high under sodium restriction. Measuring angiotensinogen and related parameters in the urine should provide clinical indicators of the activity of this paracrine tubular RAS. Not only should these correlate with sodium status, but they may also serve as markers of sodium sensitivity. Indeed, the hypothesis derived from work on A(−6) AGT mutation is that individuals homozygous for this variant would tend to maintain greater AGT expression under a high sodium diet than would individuals of other genotypes. This modest differential in the ability to down-regulate AGT under excess sodium would account for a relative propensity to retain more sodium, with long-term attendant effects on blood pressure. This would account for sodium sensitivity in these individuals. Not only could A(−6) genotype serve as a marker of this liability, as claimed earlier, but also, it is more likely that urinary parameters reflecting the activity of this newly identified paracrine tubular RAS may prove of clinical value to identify sodium sensitive individuals. These individuals would stand a higher risk of developing essential hypertension when confronted with the high sodium diet characteristic of affluent societies.

Certain parameters of the paracrine RAS can be measured in urine, specifically A-I, ANG, des-AI-ANG, and active renin (ANG denotes uncleaved, entire angiotensinogen protein, des-AI-ANG is the complement of the ANG protein after AI has been cleaved; as the peptide AI is expected to be less stable and to degrade rapidly, ANG + des-AI-ANG reflect the total amount of ANG produced in proximal tubule). These parameters reflect an individual's sodium status, as ANG and renin are down-regulated or up-regulated under high or low sodium, respectively. An individual can be classified as sodium sensitive if levels of AI, ANG, or des-AI-ANG are elevated under high salt diet compared to a reference series of individuals. The parameters names above may correlate to genetic predisposition to essential hypertension measured by AGT genotypes (M/T235 or A/G(−6)). These parameters may also be of diagnostic value in a number of clinical instances, including minimal renal disease, diabetic nephropathy, IgA nephropathy, and disorders likely to affect the function of the paracrine tubular RAS described in this application.

EXAMPLES

The present invention is described by reference to the following Examples, which are offered by way of illustration and is not intended to limit the invention in any manner. Standard techniques well known in the art or the techniques specifically described below were utilized.

Example 1

Experimental Procedures

1. Generation of antibodies. Polyclonal antiserum was raised in rabbits against highly purified mouse submaxillary gland renin according to Misono (50) and Geoghegan (51). 1:400–1:800 dilutions were used for immunohistochemistry. The antiserum recognized submaxillary gland renin (ren-2) in crude salivary gland extracts and in purified fractions, ren-1 transiently expressed in COS-1 cells, as well as prorenin from crude kidney lysates and it did not cross-react with purified cathepsin D, total COS-1 lysates or crude liver extracts.

Polyclonal antiserum for mouse Ang was raised in rabbits against highly purified mouse Ang purified as a glutathione-S-transferase (GST) fusion protein (pGX-2T expression system, Pharmacia, New Jersey, N.Y.). Ang was purified by glutathione affinity chromatography, GST-tag removal, anion-exchange, and gel permeation chromatography. 1:400 to 1:1200 dilutions were used for immunohistochemistry.

2. In vitro Ang secretion studies. tsMPT were cultured as described previously (19). tsMPT cells were grown on semi-porous membranes, media were concentrated by spin dialysis. Ang in cell medium or urine samples was measured as the release of A-I in a renin cleavage reaction (2.5 nM renin in 25 mM NaOAc, pH 6.5, 0.5 mM AEBSF, 0.5 mM 8-hydroxyquinoline, 5 mM EDTA). Generated A-I was measured with a competitive RIA (NEN DuPont, Boston, Mass.). Transepithelial resistance across the cell monolayer was assayed using microelectrodes. Diffusion of tritiated mannitol from the apical into the basolateral chamber was used to measure integrity of the cellular monolayer. Blank filters and filters with non-continuous cell monolayers served as controls. After subtraction of the electrical resistance of a blank filter, the transepithelial resistance values were 70 $\Omega/cm^2$ for an intact complete monolayer and 30 $\Omega/cm^2$ for a non-continuous monolayer.

3. Animal experiments and measurements. C57BL6 mice were used following IRB approved protocols. Twenty-four hours prior to dietary sodium manipulations, all animals were fasted with free access to water, supplemented with 2% glucose and 0.1% KCl. Either one mg/kg amiloride and 2 mg/kg furosemide (52) or control carrier were applied by subcutaneous injection. Low sodium (0.3% sodium) and high sodium (6%) diets were purchased from Purina Mills (Purina Mills Inc., St. Louis, Mo.). Blood was collected by cardiac puncture. Spot urine was collected by bladder puncture. Hemidissected kidneys were formalin-fixed or snap-frozen in liquid nitrogen. For urine collection, mice were placed in metabolic cages (Nalgene, Nalge Nunc International, Rochester, N.Y.). Urine specimens were collected at 12h intervals in tubes containing AEBSF and 8-hydroxyquinoline (NEN-DuPont, Boston, Mass.). Weight and urine volumes were recorded daily. Urinary Ang and A-I measurements were corrected for creatinine or expressed as total urinary Ang. RNA isolation and RT-PCR were performed following standard protocols (QIAGEN, Valencia, Calif.). RT-PCR experiments were performed using the Access RT-PCR system (Promega, Madison, Wis.).

4. In situ RT-PCR. In situ RT-PCR was performed as described by Ertsey and Scavo (53). Digoxigenin-labeled PCR product was detected in situ using an alkaline phosphatase conjugated anti-digoxigenin antibody (Roche, Indianapolis, Ind.) and visualized by adding the substrates nitroblue-tetrazolium and 5-bromo-4-chloro-3-indoyl-phosphate (NBT/BCIP; Sigma, St. Louis, Mo.). Sections were counterstained with PAS and photographed.

5. Immunohistochemistry. Immunostaining was performed following standard protocols (DAKO Co., Carpinteria, Calif.). The biotinylated secondary antibody was detected using streptavidin conjugated with horseradish peroxidase or alkaline phosphatase and visualized with either 3-amino-9-ethyl-carbazole (AEC; Sigma) or NBT/BCIP, respectively. Sections visualized with AEC were counterstained with hematoxylin and eosin.

6. Quantitative histology. Renin expression in renal tubular cells as a function of sodium diet, or diuretics, was assayed by quantitating the frequency of renin immunostaining in segments of the distal nephron using the peroxidase reporter enzyme and AEC chromogen. Two independent blinded investigators scored sagittal kidney for renin using a subjective 0–4 scale: 0 equaled no tubular renin staining; 1 equaled at least one positive cell per tubule segment; 2 equaled between 25–50% of cells per of tubule segment; 3 equaled more than 50% of cells per tubule segment stained for renin; 4 equaled>75%. Concordance was reproducibly greater than 90%. Four separate experiments were performed. Results were analyzed by comparing the mean±S.E.M. between groups using unpaired t-tests. $p<0.05$ was considered significant.

7. Cell Immunoblotting. Arcades of connecting tubules were microdissected following limited collagenase digestion and isolated. The purity of the isolated junctions was checked by microscopy. Isolated junctions were further collagenase digested to obtain single cells (0.5% at 37° C. for 10 min). Cells were washed and resuspended in 30 µl low sodium containing tissue culture medium (serum free DMEM), dropped on a PVDF membranes (MultiScreen-IP, 0.45 µm Hydrophobic, High Protein Binding Immobilon-P membrane Millipore Brdford, Mass.) and incubated overnight. CHO cells transfected with mouse renin and human Ang served as positive and negative control. Immunoblotting was performed as described previously (22–24). Following overnight incubation, cells were fixed on the membrane using 4% paraformaldehyde. Anti-mouse renin antibody, biotinylated anti-mouse IgG (DAKO Corporation, Carpenteria, Calif.), and streptavidine alkaline-phosphatase (DAKO) were used at 1:500 dilutions. Alkaline-phosphatase was detected using the NBT/BCIP (Sigma) chromogen. Membranes were mounted and photographed.

Example 2

Proximal Tubule Epithelium Secretes Ang at its Apical Side

Figure 1B:
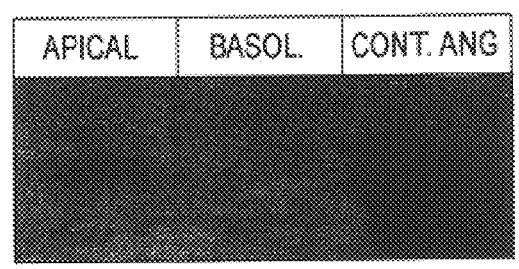

Angiotensinogen expression in whole kidney tissue was examined by immunohistochemistry in sodium restricted animals. Staining was observed only in proximal tubules, and the granular appearance of the protein was in the vicinity of their PAS-counterstained brush-border rich luminal membranes suggesting a secretory process (FIG. 1A). To test this hypothesis, confluent monolayers of conditionally immortalized cells of murine proximal tubule (19) were grown on semipermeable membranes, which separated apical and basolateral compartments. The integrity of the monolayers was established by visual inspection, by demonstration of a significant transepithelial resistance, and by monitoring the diffusion of tritiated mannitol placed in the apical chamber. Using intact monolayers, Ang was reproducibly detected in the apical but not in the basolateral compartment (FIG. 1B). Under our prevailing experimental conditions, AGT mRNA was detected by Northern blot of total RNA (19) while renin mRNA was too close to the detection limits of RT-PCR to be conclusive.

Figure 1C:
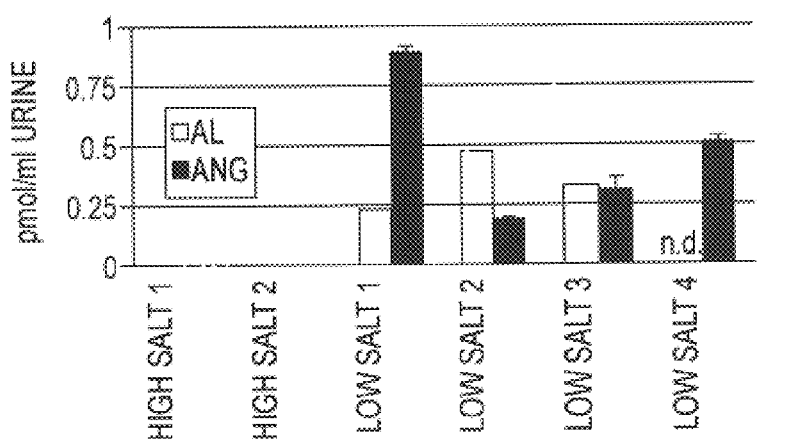
Figure 1D:
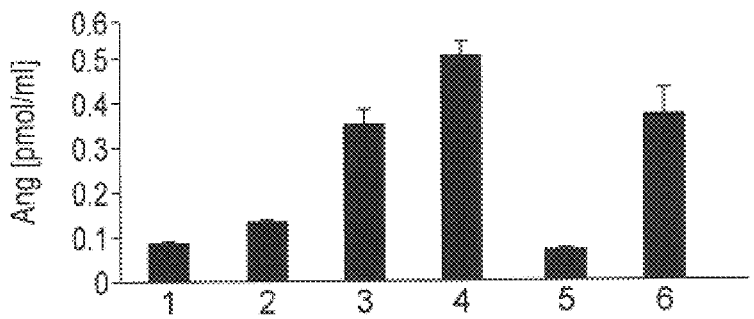

If Ang is secreted in tubular lumen, is it present in final urine? Indeed, the protein was detected in the urine of mice and men by Western Blot analysis with specific polyclonal antiserum. Native Ang was measured in 12 h-urine of male mice kept in metabolic cages with unrestricted access to food and water, conditions that did not significantly affect body weight and therefore total body water. Urinary Ang was inversely related to dietary sodium (FIG. 1C). Native Ang was also observed in urine specimens of healthy human volunteers at concentrations ranging from 66±7 to 523±33 pM (FIG. 1D).

Example 3

Renin Is Synthesized by Principal Cells of Connecting Tubule

Transit of Ang through the entire nephron reflects either elimination, delivery to a downstream site of renin expression, or both. To address this issue, the distribution of renin in the kidney was examined by immunohistochemistry with an antiserum raised against purified submaxillary gland renin (ren-2). As expected, intense staining was observed in JGA (FIG. 2B, arrow). In sodium restricted animals, staining was also observed unambiguously in the mid-cortical arcades formed by connecting segments of mid cortical and deep nephrons, but not in other segments (FIGS. 2A, B). The specificity of renin staining was confirmed by several observations. Staining was absent in sections treated with preimmune rabbit serum or after preincubation with antigen (FIG. 2D). Furthermore, our observations were confirmed using a previously established polyclonal renin antiserum (20). For each antiserum, renin immunoreactivity was jointly observed in JGA and cortical segments of distal nephron over the entire dilution series tested. Immunoreactive renin was also detected in similar segments of human kidneys using anti-human renin antiserum (FIG. 2E) (20).

Segments of the nephron distal to the macula densa can be subdivided into distinct entities on the basis of anatomical and functional features. Contrary to proximal segments, distal segments exhibit significant cellular heterogeneity. In addition to intercalated cell, distal segments have variable numbers of principal cells with features and functions that vary among segments. Cortical distal segments include the distal convoluted tubule (DCT), connecting tubule (CNT), and cortical collecting duct (CCD). The topographical distribution of tubular renin immunostaining supports the conclusion that it is present mainly in CNT segments on the basis of the following arguments: (1) staining is not observed in the larger cortical collecting ducts; (2) cellular staining is observed in cross- and longitudinal- sections of tubules in the cortical labyrinth located in the immediate vicinity of cortical radial veins (FIGS. 1A, B); (3) these clusters are only observed in the midcortical labyrinth demarcated by medullary rays. This topographical arrangement is characteristic of the arcades formed by merging connecting tubules of midcortical and deep nephrons (21).

The epithelium of connecting tubules is composed of two main cell types. The intercalated cells (IC) are subdivided into two subtypes, α and β; both express $H^+$-ATPase, whereas only the β subtype stains for peanut lectin. Staining of serial sections for renin, $H^+$-ATPase (FIGS. 2F, G) or peanut lectin revealed that cells staining for renin did not stain for $H^+$-ATPase or peanut lectin, suggesting that they are not IC. The morphology of renin-positive cells is consistent with that reported for cortical connecting tubule (CNT) cells, with a characteristic polygonal appearance, with a convex apical side devoid of brush border, and a centrally located nucleus within an abundant clear cytoplasm (21). Notably, renin staining predominates in the apical segment of the cytoplasm and in the vicinity of the nucleus.

Figure 3A:
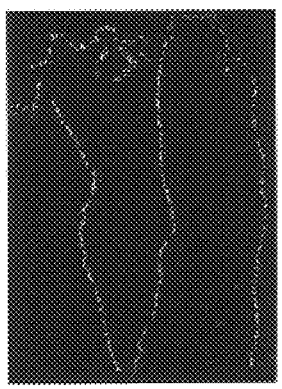
FIGS. 3A–3E demonstrate de novo renin synthesis in the connecting tubule (CNT). Graphic reconstruction of a microdissected nephron is shown in FIG. 3A, with close-ups of a proximal convoluted tubule (FIG. 3B), glomerulus and macula densa (FIG. 3C), and midcortical CNT arcade (FIG. 3D).
Figure 3B:
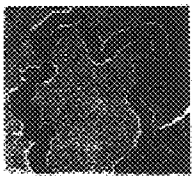
Figure 3C:
Figure 3D:
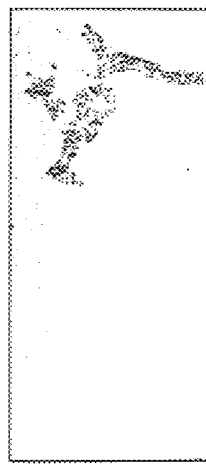
Figure 3E:
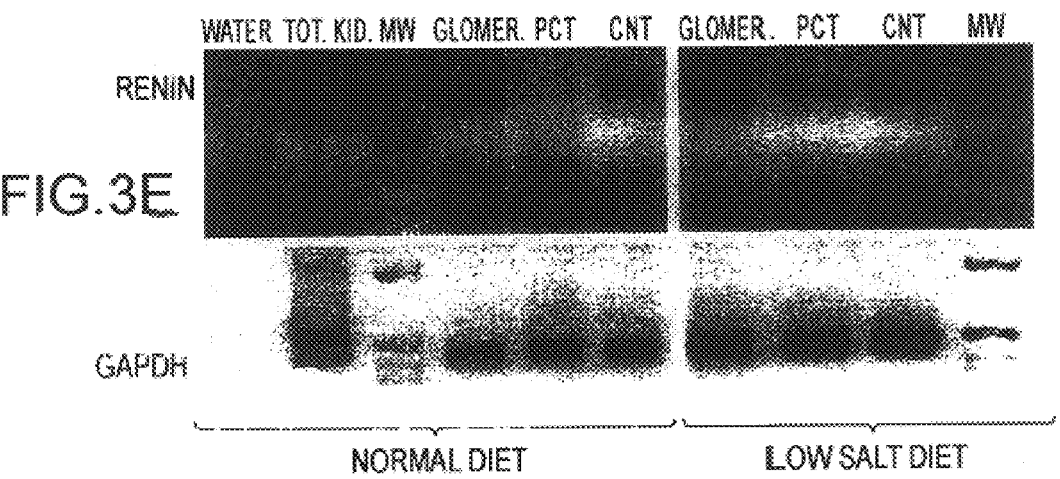
Figure 3F:
FIGS. 3F–3K demonstrate de novo renin synthesis in the connecting tubule (CNT), showing localization of renin expression in CNT cells by in situ RT-PCT. These figures are representative of four independent replicate experiments.
Figure 3G:

The hypothesis of local renin synthesis, as opposed to uptake of renin of systemic or proximal tubular origin, was tested by a combination of microdissection of connecting tubule arcade and RT-PCR. During microdissection, glomeruli (FIGS. 3A, C), proximal convoluted tubules (FIGS. 3A, B) loops of Henle and blood vessels were readily identifiable and separated from arcade junctions between connecting tubules and either connecting tubules or cortical collecting ducts (FIGS. 3A, D). Renin amplification products of expected size and sequence were clearly observed in RNA preparations from glomerulus independently of dietary sodium (FIG. 3E). Unambiguous signal was also observed in isolated connecting tubule arcades particularly in sodium restricted animals. Only minimal signal was noted in proximal tubule under sodium restriction. These observations were reproduced in four independent series of microdissection experiments. Controls included amplification of GAPDH for RNA quality and α-smooth muscle actin to exclude contamination of tubular segments with JGA components. The specificity of all amplification products was confirmed by DNA sequencing.

Figure 3H:
Figure 3I:
Figure 3J:
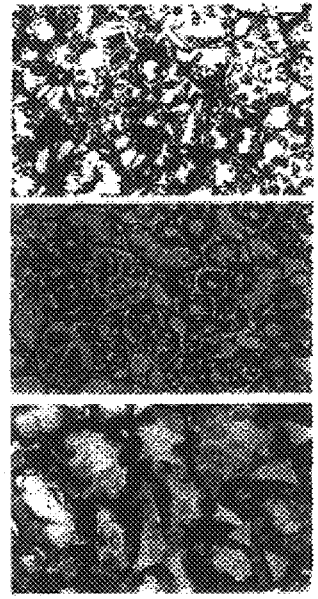
Figure 3K:

To confirm renin synthesis in connecting tubules of the nephron by an independent method, in situ RT-PCR was applied to kidney sections from mice subjected to 16-hour sodium restriction (FIGS. 3F–K). Renin mRNA was unambiguously identified in cells of cortical segments of the distal nephron and in cells of afferent arterioles (FIGS. 3I–K). Renin mRNA was not detected in proximal tubules (FIGS. 3I, J arrowhead). Nor was it detected in the inner or outer medulla. Control sections not pretreated with DNase showed uniform staining of all cells in all nephron segments (FIGS. 3F, G); control sections, DNase treated but not reverse transcribed, showed no staining (FIG. 3H). Further evidence of specificity was provided by the absence of signal when primers were applied to samples that were not reverse transcribed. The specificity of the primers used for amplification was validated by DNA sequencing in control RT-PCR experiments. To further ensure that amplification was specific and not the result of primer extension of fragmented genomic DNA, control amplifications were performed from reaction supernatants.

Example 4

CNT Cells Secrete Renin

Figure 3L:
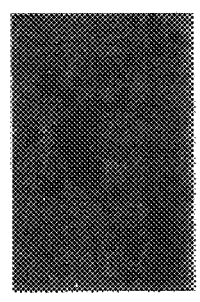
FIGS. 3L–3M demonstrate de novo renin synthesis in the connecting tubule (CNT), showing renin secretion by CNT cells.
Figure 3M:
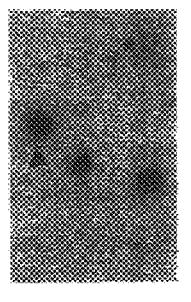
Figure 3N:
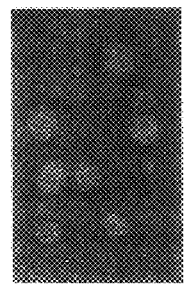
In FIG. 3N, CHO cells expressing angiotensinogen served as negative control.

Renin secretion by CNT cells was demonstrated using cell immunoblotting (22–24). Isolated cells from microdissected arcades of connecting tubules secreted renin (FIG. 3L). CHO cells expressing mouse renin (FIG. 3; M) and human angiotensinogen (FIG. 3; N) served as positive and negative control respectively. Renin secretion was revealed by pericellular halos of immunoreactive renin.

Example 5

Renin Expression in CNT Varies with Dietary Sodium

Figure 4A:
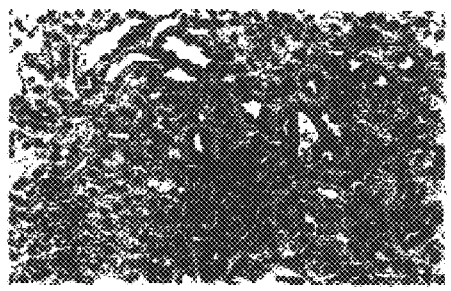
FIGS. 4A–4E show variation in renin expression in CNT cells of midcortical and deep nephrons as a function of sodium load and distal sodium delivery.
Figure 4B:
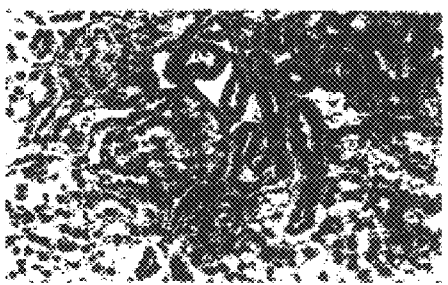
Figure 4C:
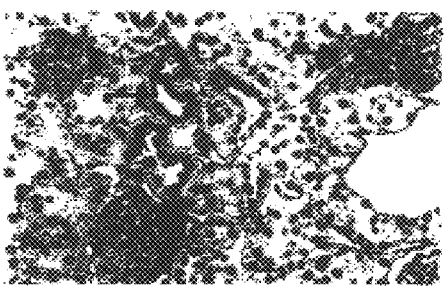
Figure 4D:
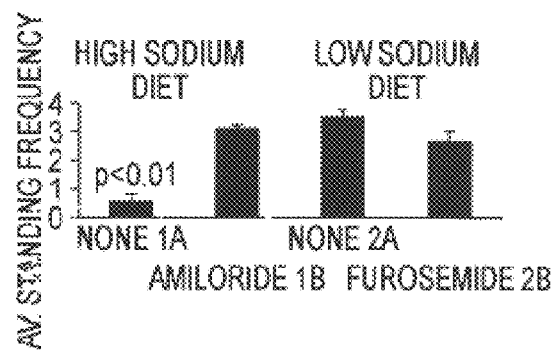
Figure 4E:
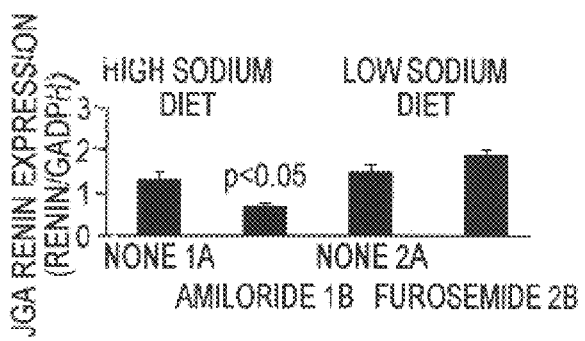

On the basis of immunostaining and expression studies, we conclude that, in addition to its major site of expression in JGA, renin is also expressed in connecting tubule. In subsequent studies, we have used renin immunostaining to investigate the relationship between dietary sodium and CNT renin after overnight manipulation of tubular sodium delivery by varying total sodium intake and/or sodium reabsorption at specific sites through diuretics. Furosemide inhibits the $Na^+/K^+2Cl^-$ transporter upstream of the distal tubule, whereas amiloride, a sodium channel blocker, affects sodium reabsorption in distal segments of the nephron. Because of signal saturation of renin immunostaining in JGA, renin expression at this site was estimated by semi-quantitative RT-PCR of total kidney RNA (25). Renin expression in CNT cells was assessed by quantitative histology (frequency of CNT cells staining for renin). Scoring was performed by two independent, blinded observers in four independent sets of replicate experiments. Under high sodium, animals exhibited minimal renin staining in CNT and moderate JGA renin expression (FIG. 4A; FIGS. 4D, E group 1A). By contrast, the combination of high sodium and amiloride administration led to a marked increase in CNT immunoreactive renin (FIG. 4B; FIGS. 4D, E group 1B); JGA renin was significantly decreased ($p<0.05$). Overnight sodium restriction led to a marked increase in CNT immunoreactive renin. (FIG. 4C, FIGS. 4D, E group 2A) but no significant change in JGA renin. However, longer periods of sodium restriction stimulated renin expression in JGA. The combination of sodium restriction and furosemide resulted in decreased renin expression in CNT, without additional effects on JGA renin (FIGS. 4D, E group 2B). Manipulation of dietary sodium was monitored by measuring total sodium excretion. Under these experimental conditions, the treatments were without effect on body weight, therefore excluding significant variation in total body water.

The observations of the present invention support the following conclusions: (1) angiotensinogen is synthesized by proximal tubule and secreted into tubular fluid; (2) uncleaved Ang transits through the entire nephron and can be found in final urine; (3) renin is synthesized and secreted by CNT cells and (4) both proximal angiotensinogen and distal renin expression vary as a function of dietary sodium. Together with filtered renin, the spatial distribution of these elements of a tubular RAS and their correlation with dietary salt suggest that they play an important role in the coordinated regulation of sodium reabsorption at various sites within the nephron.

The presence of AGT mRNA in proximal tubule and its variation with sodium intake has been observed previously in whole kidney sections (5). Besides confirming these findings, the data presented herein characterize the time-course of AGT expression in parallel with that of renin in distal segments of the nephron and with the urinary excretion of Ang and A-I. Furthermore, they demonstrate luminal secretion of Ang by polarized epithelium; previous experiments with primary culture of heterogeneous cell populations from kidney cortex suggested secretion of the protein but could not resolve the directionality of this process (26). The observations concerning urinary Ang confirm prior reports using laboratory animals (27–29). In the past, urinary angiotensinogen was thought to be a clinical indicator of damage to the glomerular membrane, since Ang is normally not filtered (30, 31).

Secretion of Ang to the apical side of cultured monolayers does not in itself provide definitive evidence for luminal secretion of the protein by proximal tubule in vivo. The apical distribution of Ang secretory granules in proximal tubule (FIG. 1A) suggests such a process. So does the presence of Ang in final urine in a direct correlation with AGT expression in proximal tubule and in an inverse relationship with dietary sodium. Taken together, these observations strongly suggest that Ang is indeed secreted in tubular fluid in this initial nephron segment. If so, filtered renin of systemic origin could act on luminal Ang to generate A-II. The functional significance of A-II as a major regulator of sodium transport in this segment, in part through its stimulation of the sodium-hydrogen exchanger, NHE-3

(9, 10, 32), is well documented (4). With this hypothesis, ultrafiltration of systemic renin would not be regarded only as an elimination route for the enzyme, as it would also serve an important function in regulating bulk sodium reabsorption in proximal tubule Previous reports have suggested the existence of an autocrine RAS in proximal tubule, primarily on the basis of the detection of renin mRNA by RT-PCR of total RNA from selected cell populations or from microdissected segments of proximal tubule (8, 33–35). The present observation of intracellular A-I and A-II formation in tsMPT and faint renin amplification product in microdissected segments of proximal tubule in sodium restricted animals are consistent with this model. The expression levels of renin and angiotensinogen in proximal tubule are markedly different, however. Angiotensinogen protein appears abundant in epithelium of proximal tubule, whereas renin is below the detection level of immunohistochemistry when antibodies are used at dilutions ensuring specificity. Likewise, AGT mRNA is detected by Northern blot of total RNA. By contrast, evidence for a renin transcript at this site escapes even in situ hybridization after RT-PCR, a faint signal appearing only in liquid-phase RT-PCR. The functional significance of the latter observation remains unclear, as faint RT-PCR signals can reflect either legitimate or illegitimate transcription. Whereas the reaction between filtered renin and secreted Ang may be the predominant mechanism of formation of A-II in tubular fluid of the proximal tubule, an autocrine or intracrine local RAS, expressed at a much lower level, may still serve a distinct purpose in the homeostasis of this nephron segment.

Renin immunoreactivity has been occasionally noted in tubular segments of mouse kidney (36–39). In one case, where the focus of the investigation was on JGA renin, it was dismissed as an experimental artifact (38). In other instances, the authors relied on indirect arguments to suggest that it represented non-specific uptake of filtered renin. In the present work, the hypothesis of local synthesis was examined directly following two distinct experimental approaches. Concordant results obtained in repeated series of four independent experiments for each of two different methods strongly support the hypothesis of local renin synthesis. The predominantly apical distribution of renin immunostaining in tissue sections (FIG. 2C) and the demonstration of renin secretion by isolated CNT cell in vitro suggests that renin is secreted into tubular lumen. The observation of renin in final urine alone does not settle this issue, however, as it cannot be excluded that some of the filtered renin of systemic origin escapes degradation in proximal tubule. Taken together, these data suggest that renin secreted by connecting tubule could act on luminal angiotensinogen that originated in proximal tubule to release A-I in luminal fluid. The documented presence of both ACE and A-II receptors in collecting duct (15, 16) would allow formation and action of A-II in distal segments of the nephron. Because of poor accessibility to direct experimental investigation, little is known about the effect of A-II in connecting tubule and collecting duct. One report does suggest that luminal A-II stimulates amiloride-sensitive sodium transport in the initial collecting tubule of cortical nephrons (11).

The distribution of renin immunostaining in connecting tubule arcades is strikingly similar to, the site of expression of tissue kallikrein in kidney. While colocalization of renin and kallikrein remains to be established, it has indeed been shown that tissue kallikrein secreted into distal tubule (40) originate in CNT (41), with predominant immunostaining at the apical side of CNT cells in a pattern quite similar to that observed here for renin (42, 43). It is also known that kininogen is synthesized and secreted in tubular lumen by principal cells of the collecting duct, and bradykinin B2 receptors have been reported at the luminal side of this nephron segment (44). The presence of components of both the renin-angiotensin and the kallikrein-kinin systems in the luminal compartment of connecting tubule and collecting duct suggests that the two systems may play a coordinated, balanced role in the fine regulation of the concentrations of sodium and potassium in final urine. These systems are interrelated not only through the often described opposite actions of their effectors, A-II and bradykinin, but also through multiple areas of potential overlap, such as aldosterone response, sodium and potassium balance, renin activation, and peptide conversion through the action of ACE. Connecting tubule would appear to be a very strategic site in this coordinated regulation.

The experimental work of Guyton and his colleagues has long established the significance of the pressure-natriuresis relationship in the regulation of baseline blood pressure, and the dominant role of intrarenal A-II in the regulation of sodium balance in response to variation in dietary sodium (45, 46). The genetics of rare mendelian hypertension such as Liddle syndrome (47) or the syndrome of mineralocorticoid excess (48, 49) confirm experimental physiology by stressing the significance of sodium reabsorption in distal segments of the nephron in blood pressure regulation. Angiotensinogen of proximal tubular origin and renin expressed by connecting tubule may provide a mechanism to coordinate the functions of proximal and distal segments of the nephron in regulation of sodium balance and blood volume homeostasis. It may be through this system that molecular variation at the AGT locus (18) affects individual liability to develop essential hypertension.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

1. Hall, J. B., MW. Intrarenal and circulating angiotensin II and renal function. in *The Renin-Angiotensin System* Vol. 1 (ed. Robertson, J., Nicholls, MG) 26.1–26.43 (Gower Medical Publishing, New York, 1993).
2. Corvol, P., Soubrier, F. & Jeunemaitre, X. Molecular genetics of the renin-angiotensin-aldosterone system in human hypertension. *Pathol Biol* (Paris) 45, 229–39 (1997).
3. Seikaly, M. G., Arant, B. S., Jr. & Seney, F. D., Jr. Endogenous angiotensin concentrations in specific intrarenal fluid compartments of the rat. *J Clin Invest* 86, 1352–7 (1990).
4. Navar, L. G., Imig, J. D., Zou, L. & Wang, C. T. Intrarenal production of angiotensin II. *Semin Nephrol* 17, 412–22 (1997).
5. Ingelfinger, J. R., Pratt, R. E., Ellison, K. & Dzau, V. J. Sodium regulation of angiotensinogen mRNA expression in rat kidney cortex and medulla. *J Clin Invest* 78, 1311–5 (1986).
6. Ingelfinger, J. R. et al. Intrarenal angiotensinogen: localization and regulation. *Pediatr Nephrol* 4, 424–8 (1990).
7. Ingelfinger, J. R., Zuo, W. M., Fon, E. A., Ellison, K. E. & Dzau, V. J. In situ hybridization evidence for angiotensinogen messenger RNA in the rat proximal tubule. An hypothesis for the intrarenal renin angiotensin system. *J Clin Invest* 85, 417–23 (1990).
8. Tank, J. E., Henrich, W. L. & Moe, O. W. Regulation of glomerular and proximal tubule renin mRNA by chronic changes in dietary NaCl. *Am J Physiol* 273, F892–8 (1997).
9. Liu, F. Y. & Cogan, M. G. Angiotensin II stimulation of hydrogen ion secretion in the rat early proximal tubule. Modes of action, mechanism, and kinetics. *J Clin Invest* 82, 601–7 (1988).
10. Cogan, M. G. Angiotensin II: a powerful controller of sodium transport in the early proximal tubule. *Hypertension* 15, 451–8 (1990).
11. Wang, T. & Giebisch, G. Effects of angiotensin II on electrolyte transport in the early and late distal tubule in rat kidney. *Am J Physiol* 271, F143–9 (1996).
12. Vos, P. F., Boer, P. & Koomans, H. A. Effects of enalapril on renal sodium handling in healthy subjects on low, intermediate, and high sodium intake. *J Cardiovasc Pharmacol* 22, 27–32 (1993).
13. Vos, P. F., Boer, P., Braam, B. & Koomans, H. A. The origin of urinary angiotensins in humans. *J Am Soc Nephrol* 5, 215–23 (1994).
14. Tojo, A., Tisher, C. C. & Madsen, K. M. Angiotensin II regulates H(+)-ATPase activity in rat cortical collecting duct. *Am J Physiol* 267, F1045–51 (1994).
15. Casarini, D. E. et al. Angiotensin I-converting enzyme activity in tubular fluid along the rat nephron. *Am J Physiol* 272, F405–9 (1997).
16. Harrison-Bernard, L. M., Navar, L. G., Ho, M. M., Vinson, G. P. & el-Dahr, S. S. Immunohistochemical localization of ANG II AT1 receptor in adult rat kidney using a monoclonal antibody. *Am J Physiol* 273, F170–7 (1997).
17. Jeunemaitre, X. et al. Molecular basis of human hypertension: role of angiotensinogen. *Cell* 71, 169–80 (1992).
18. Inoue, I. et al. A nucleotide substitution in the promoter of human angiotensinogen is associated with essential hypertension and affects basal transcription in vitro. *J Clin Invest* 99, 1786–97 (1997).
19. Loghman-Adham, M. et al. A conditionally immortalized cell line from murine proximal tubule. *Kidney Int* 52, 229–39 (1997).
20. Yokosawa, H., Yokosawa, N. & Inagami, T. Specific antibody to human renal renin and its cross-reactivity with inactive human plasma prorenin. *Proc Soc Exp Biol Med* 164, 466–70 (1980).
21. Kaissling, B. & Kriz, W. Morphology of the loop of Henle, distal tubule, and collecting duct. in *Handbook of Physiology, Section 8: Renal Physiology* Vol. 8 (ed. Winhager, E.) 109–167 (Oxford University Press, Oxford, 1992).
22. Chiou, C. Y., Williams, G. H. & Kifor, I. Study of the rat adrenal renin-angiotensin system at a cellular level. *J Clin Invest* 96, 1375–81 (1995).
23. Kendall, M. E. & Hymer, W. C. Cell blotting: a new approach to quantify hormone secretion from individual rat pituitary cells. *Endocrinology* 121, 2260–2 (1987).
24. Kendall, M. E. & Hymer, W. C. Measurement of hormone secretion from individual cells by cell blot assay. *Methods Enzymol* 168, 327–38 (1989).
25. Rupp, R. A. & Weintraub, H. Ubiquitous MyoD transcription at the midblastula transition precedes induction-dependent MyoD expression in presumptive mesoderm of X. laevis. *Cell* 65, 927–37 (1991).
26. Yanagawa, N. et al. Production of angiotensinogen and renin-like activity by rabbit proximal tubular cells in culture. *Kidney Int* 39, 938–41 (1991).
27. Wang, T. T. et al. Isoproterenol and 8-bromo-cyclic adenosine monophosphate stimulate the expression of the angiotensinogen gene in opossum kidney cells. *Kidney Int* 46, 703–10 (1994).
28. Yoshiya, M., Tsutsui, Y., Itoh, N. & Okamoto, H. Angiotensinogen excretion in rat urine: effects of lipopolysaccharide treatment and sodium balance. *Jpn J Pharmacol* 57, 37–44 (1991).
29. Yang, G., Merrill, D. C., Thompson, M. W., Robillard, J. E. & Sigmund, C. D. Functional expression of the human angiotensinogen gene in transgenic mice. *J Biol Chem* 269, 32497–502 (1994).
30. Favaro, S. et al aL Urinary angiotensinogen loss in chronic proteinuric glomerulonephritis. *Int Urol Nephrol* 4, 195–8 (1972).
31. Tewksbury, D. Angiotensinogen: Biochemistry and Molecular Biology. in *Hypertension: Pathophysiology, Diagnosis, and Management* Vol. 1 (ed. Laragh, J., Brenner, BM) 1197–1216 (Raven Press, New York, 1990).
32. Moe, O. W. Sodium-hydrogen exchange in renal epithelia: mechanisms of acute regulation. *Curr Opin Nephrol Hypertens* 6, 440–6 (1997).
33. Moe, O. W. et al. Renin expression in renal proximal tubule. *J Clin Invest* 91, 774–9 (1993).
34. Henrich, W. L., McAllister, E. A., Eskue, A., Miller, T. & Moe, O. W. Renin regulation in cultured proximal tubular cells. *Hypertension* 27, 1337–40 (1996).
35. Tank, J. E., Moe, O. W., Star, R. A. & Henrich, W. L. Differential regulation of rat glomerular and proximal tubular renin mRNA following uninephrectomy [published errata appear in *Am J Physiol* July 1996; 271(1 Pt 2): section F following table of contents and December 1996; 271(6 Pt 3):section F following table of contents]. *Am J Physiol* 270, F776–83 (1996).
36. Taugner, R., Hackenthal, E., Inagami, T., Nobiling, R. & Poulsen, K. Vascular and tubular renin in the kidneys of mice. *Histochemistry* 75, 473–84 (1982).
37. Taugner, R. et al. The intrarenal renin-angiotensin-system. An immunocytochemical study on the localization of renin, angiotensinogen, converting enzyme and the angiotensins in the kidney of mouse and rat. *Klin Wochenschr* 60, 1218–22 (1982).
38. Celio, M. R. & Inagami, T. Renin in the human kidney. Immunohistochemical localization. *Histochemistry* 72, 1–10 (1981).
39. Taugner, R. et al. Coexistence of renin and angiotensin II in epitheloid cell secretory granules of rat kidney. *Histochemistry* 81, 39–45 (1984).
40. Scicli, A. G., Carretero, O. A., Hampton, A., Cortes, P. & Oza, N. B. Site of kininogenase secretion in the dog nephron. *Am J Physiol* 230, 533–6 (1976).
41. Omata, K., Carretero, O. A., Scicli, A. G. & Jackson, B. A. Localization of active and inactive kallikrein (kininogenase activity) in the microdissected rabbit nephron. *Kidney Int* 22, 602–7 (1982).
42. Figueroa, C. D., Caorsi, I., Subiabre, J. & Vio, C. P. Immunoreactive kallikrein localization in the rat kidney: an immuno-electron-microscopic study. *J Histochem Cytochem* 32, 117–21 (1984).
43. Vio, C. P. & Figueroa, C. D. Evidence for a stimulatory effect of high potassium diet on renal kallikrein. *Kidney Int* 31, 1327–34 (1987).
44. Tomita, K. & Pisano, J. J. Binding of [3H]bradykinin in isolated nephron segments of the rabbit. *Am J Physiol* 246, F732–7 (1984).
45. Guyton, A. C. Blood pressure control—special role of the kidneys and body fluids. *Science* 252, 1813–6 (1991).

46. Guyton, A. C. Kidneys and fluids in pressure regulation. Small volume but large pressure changes. *Hypertension* 19, I2–8 (1992).
47. Shimkets, R. A. et al. Liddle's syndrome: heritable human hypertension caused by mutations in the beta subunit of the epithelial sodium channel. *Cell* 79, 407–14 (1994).
48. Mune, T., Rogerson, F. M., Nikkila, H., Agarwal, A. K. & White, P. C. Human hypertension caused by mutations in the kidney isozyme of 11 beta-hydroxysteroid dehydrogenase. *Nat Genet* 10, 394–9 (1995).
49. White, P. C., Mune, T., Rogerson, F. M., Kayes, K. M. & Agarwal, A. K. 11 beta-Hydroxysteroid dehydrogenase and its role in the syndrome of apparent mineralocorticoid excess. *Pediatr Res* 41, 25–9 (1997).
50. Misono, K. S., Holladay, L. A., Murakami, K., Kuromizu, K. & Inagami, T. Rapid and largescale purification and characterization of renin from mouse submaxillary gland. *Arch Biochem Biophys* 217, 574–81 (1982).
51. Geoghegan, K. F. et al. Simple procedure for recovery of crystallizable human recombinant renin from mammalian cell-conditioned medium. *Adv Exp Med Biol* 306, 379–81 (1991).
52. Ingelfinger, J. R. et al. Intrarenal angiotensinogen: localization and regulation. *Pediatr Nephrol* 4, 424–8.
53. Ertsey, R. & Scavo, L. M. Coverslip mounted-immersion cycled in situ RT-PCR for the localization of mRNA in tissue sections. *Biotechniques* 24, 92, 94, 96, 98–100 (1998).

What is claimed is:

1. A method for determining the sensitivity of an individual to sodium, wherein sodium sensitivity is defined as an individual's tendency to respond to excess sodium intake with an increase in blood pressure, said method comprises measuring the amount of a substance selected from the group consisting of angiotensinogen, angiotensin-I and des-angiotensin-I-angiotensinogen in the urine of an individual under normal physiological conditions except said individual is on a high salt diet and comparing said amount with a reference standard, wherein an elevated amount of said substance in an individual on a high salt diet under normal physiological conditions is indicative of sodium sensitivity.

2. A method for assessing the function of the renal proximal tubule in an individual, which comprises measuring the amount of a substance selected from the group consisting of angiotensinogen, angiotensin-I and des-angiotensin-I-angiotensinogen and renin in the urine of an individual under normal physiological conditions and said individual is not on a high salt diet and comparing said amount with a reference standard, wherein an elevated amount of said substance in an individual under normal physiological conditions is indicative of a higher tubular flow and a reduced amount of said substance in an individual under normal physiological conditions is indicative of a lower tubular flow.

* * * * *